US 6,562,968 B2
(12) United States Patent
Zhou et al.

(10) Patent No.: US 6,562,968 B2
(45) Date of Patent: May 13, 2003

(54) METHOD OF PURIFYING TETRODOTOXIN

(75) Inventors: Maoqing Zhou, Nanning (CN); Frank Hay Kong Shum, North Vancouver (CA)

(73) Assignee: Nanning Maple Leaf Pharmaceutical Co., Ltd., Nanning (CN)

( * ) Notice: Subject to any disclaimer, the term of this patent is extended or adjusted under 35 U.S.C. 154(b) by 18 days.

(21) Appl. No.: 09/818,863

(22) Filed: Mar. 28, 2001

(65) Prior Publication Data

US 2002/0099226 A1 Jul. 25, 2002

(51) Int. Cl.[7] .............................................. C07D 239/00
(52) U.S. Cl. ........................ 544/245; 544/247; 544/250
(58) Field of Search ................................ 544/245, 247, 544/250

(56) References Cited

U.S. PATENT DOCUMENTS

| | | | |
|---|---|---|---|
| 4,857,653 A | 8/1989 | Colin et al. | 549/511 |
| 4,924,011 A | 5/1990 | Denis et al. | 549/510 |
| 5,019,504 A | 5/1991 | Christen et al. | 435/123 |
| 5,336,785 A | 8/1994 | Holton | 549/214 |
| 5,451,392 A | 9/1995 | Strobel et al. | 549/510 |
| 5,475,120 A | 12/1995 | Rao | 549/510 |
| 5,478,736 A | 12/1995 | Nair | 435/123 |

OTHER PUBLICATIONS

Xinfu Pan et al., "Advances in the Study of Tetrodotoxin", Aquatic Product Institute of Hebei, pp. 1–8 (1979).
Hashimoto, "Marine Toxins and Other Bioactive Marine Metabolites", pp. 71–91 c. 1979 by Japan Society Press.
Zhao et al., China J. Hygiene Examination, vol. 49, pp. 263–265 (1994).
Yamamoto et al., Agric. Biol. Chem., vol. 49, pp. 3077–80 (1985).
Goto et al., Tetrahedron, vol. 21, pp. 2059–88 (1965).
Nakamura et al., Toxicon, vol. 23, pp. 271–276 (1985).
Goto et al., J. Chem. Soc. Japan, vol. 85, pp. 2–9 (1964).
H. Kakisawa et al., J. Chem. Soc. Japan, vol. 80, pp. 1483–1487 (1959) (abstract from Chem. Abstr. vol. 55, pp. 3542).
A. Yokoo et al., J. Chem. Soc. Japan, vol. 71, pp. 590–592 (1950) (abstract from Chem. Abstr. vol. 45, pp. 6760).

*Primary Examiner*—Amelia Owens
(74) *Attorney, Agent, or Firm*—Birch, Stewart, Kolasch & Birch, LLP

(57) ABSTRACT

The present invention relates to a new process of purifying tetrodotoxin using high performance liquid chromatograph technology.

11 Claims, 25 Drawing Sheets

Figure 3. HPLC profile of crude TTX (Batch 990705)

Channel A

| Time | Area | Area % | Height | Height % |
|---|---|---|---|---|
| 7.408 | 9871 | 1.07 | 473 | 1.03 |
| 9.917 | 798671 | 86.44 | 41760 | 90.77 |
| 12.815 | 3131 | 0.34 | 161 | 0.35 |
| 14.593 | 107170 | 11.60 | 3441 | 7.48 |
| 15.611 | 5068 | 0.55 | 172 | 0.37 |
| Totals | 923912 | 100.00 | 46007 | 100.00 |

Figure 4. HPLC profile of TTX reference (Sample 1)

Channel A

| Time | Area | Area % | Height | Height % |
|---|---|---|---|---|
| 6.285 | 23224 | 0.52 | 1269 | 0.91 |
| 8.812 | 7279 | 0.16 | 323 | 0.23 |
| 10.663 | 5406 | 0.12 | 253 | 0.18 |
| 12.454 | 4471109 | 99.20 | 137177 | 98.67 |

| Totals | | | | |
|---|---|---|---|---|
| | 4507019 | 100.00 | 139023 | 100.00 |

Figure 5. HPLC profile of TTX reference (Sample 1)
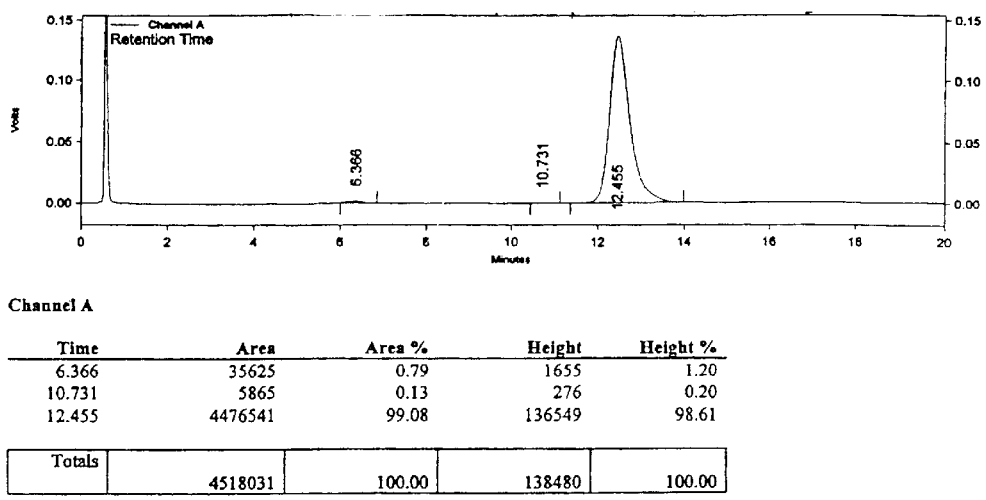
Channel A
| Time | Area | Area % | Height | Height % |
|---|---|---|---|---|
| 6.366 | 35625 | 0.79 | 1655 | 1.20 |
| 10.731 | 5865 | 0.13 | 276 | 0.20 |
| 12.455 | 4476541 | 99.08 | 136549 | 98.61 |
| Totals | | | | |
|---|---|---|---|---|
| | 4518031 | 100.00 | 138480 | 100.00 |

Figure 6. HPLC profile of TTX reference (Sample 2)
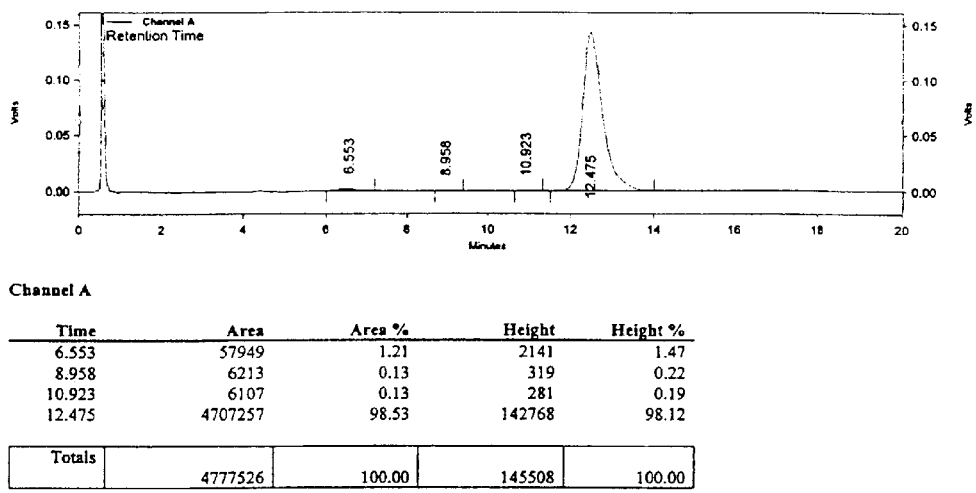
Channel A
| Time | Area | Area % | Height | Height % |
|---|---|---|---|---|
| 6.553 | 57949 | 1.21 | 2141 | 1.47 |
| 8.958 | 6213 | 0.13 | 319 | 0.22 |
| 10.923 | 6107 | 0.13 | 281 | 0.19 |
| 12.475 | 4707257 | 98.53 | 142768 | 98.12 |
| Totals | | | | |
|---|---|---|---|---|
| | 4777526 | 100.00 | 145508 | 100.00 |

Figure 7. HPLC profile of TTX reference (Sample 2)

Channel A

| Time | Area | Area % | Height | Height % |
|---|---|---|---|---|
| 12.476 | 4701155 | 99.95 | 142382 | 99.91 |
| 14.334 | 2136 | 0.05 | 123 | 0.09 |

| Totals | | | | |
|---|---|---|---|---|
| | 4703292 | 100.00 | 142505 | 100.00 |

Figure 8. HPLC profile of TTX (Batch 990224)
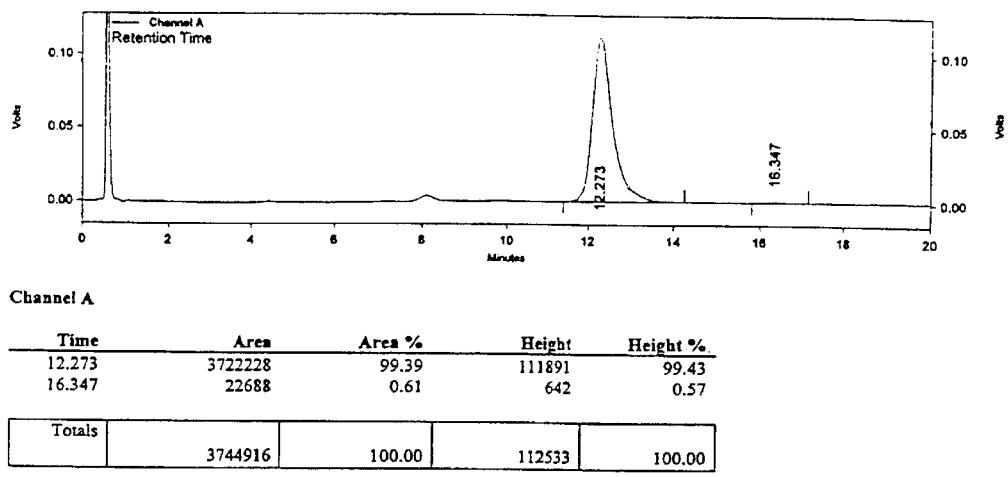

Figure 9. HPLC profile of TTX (Batch 990224)
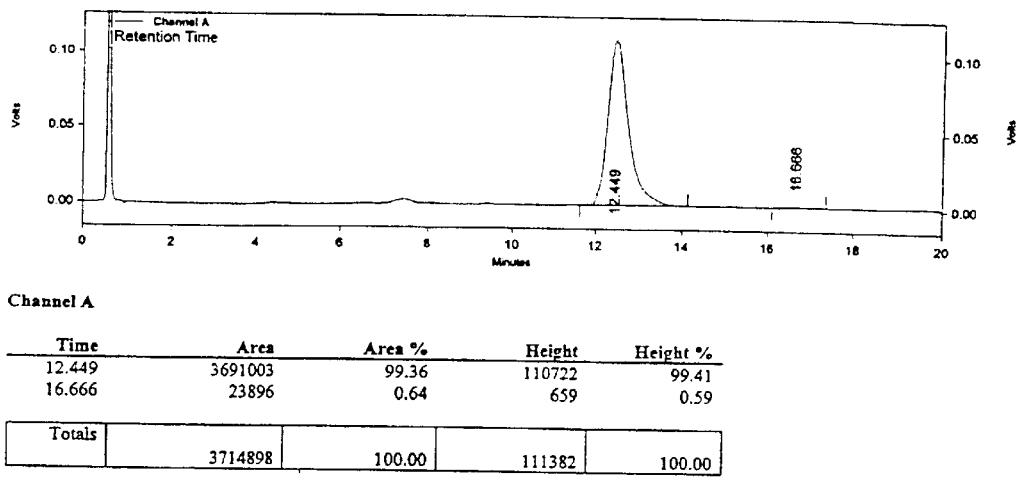

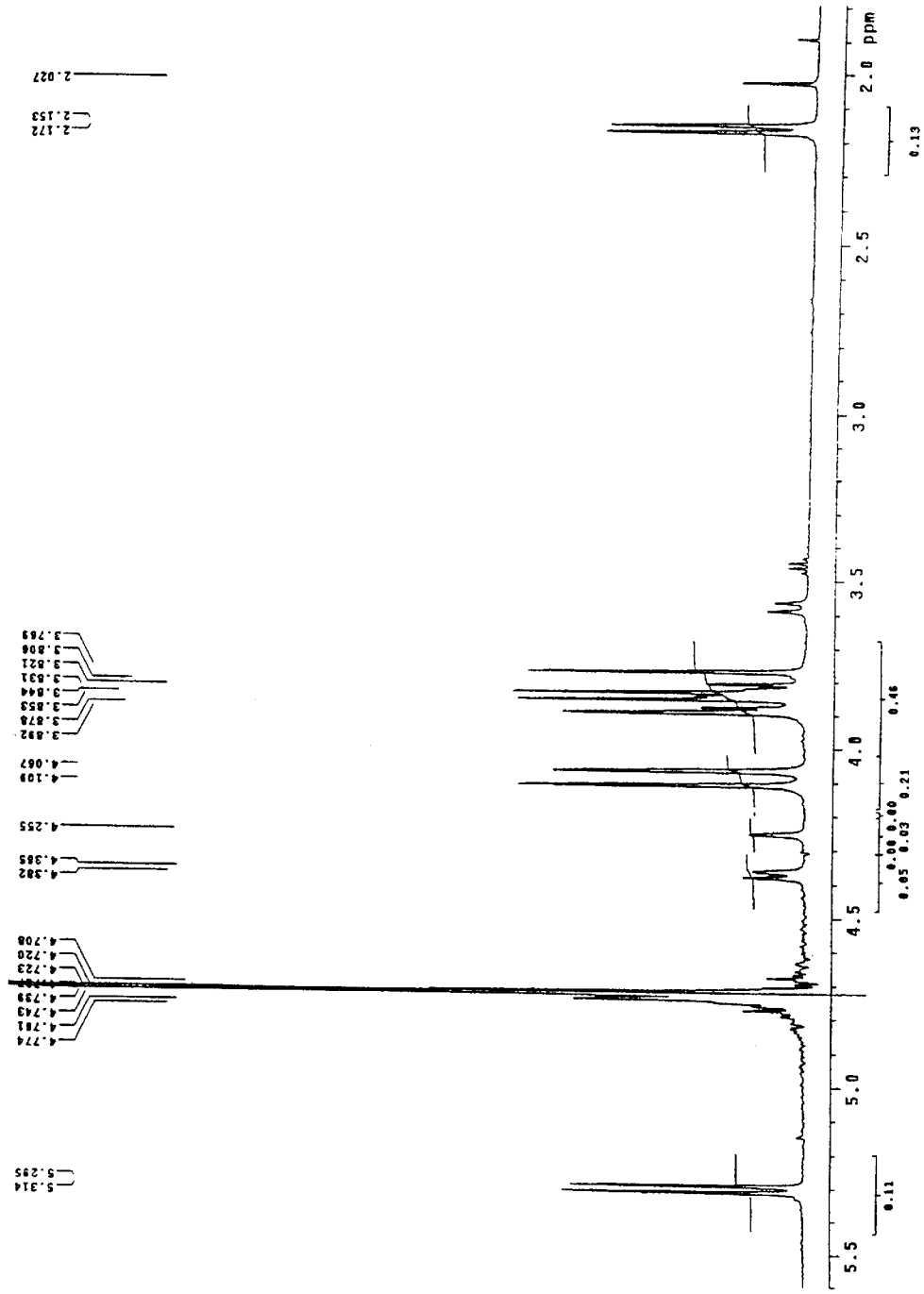
Figure 10. $^1$H-NMR spectrum of TTX (Batch 990224)

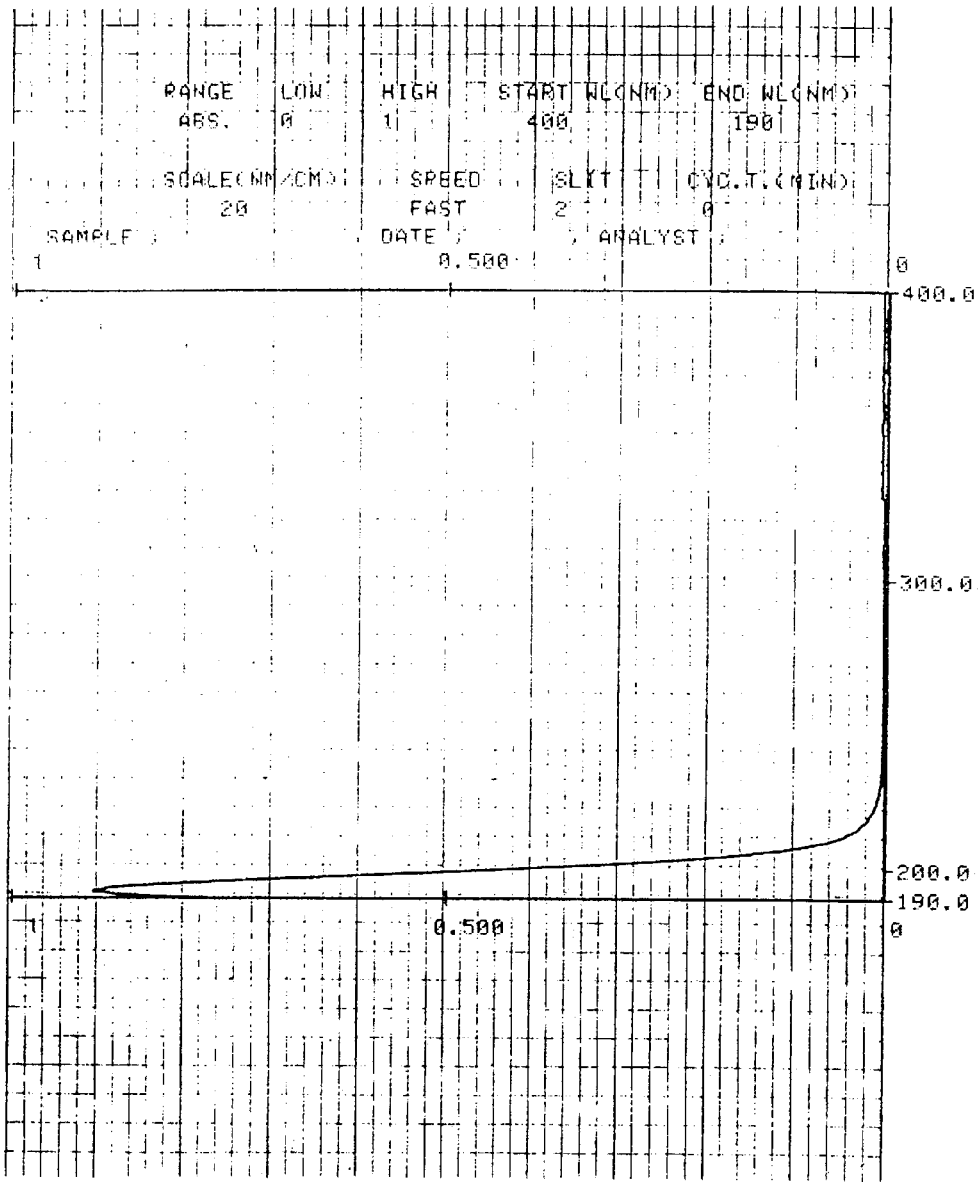
Figure 11. UV absorption spectrum of TTX (Batch 990224)

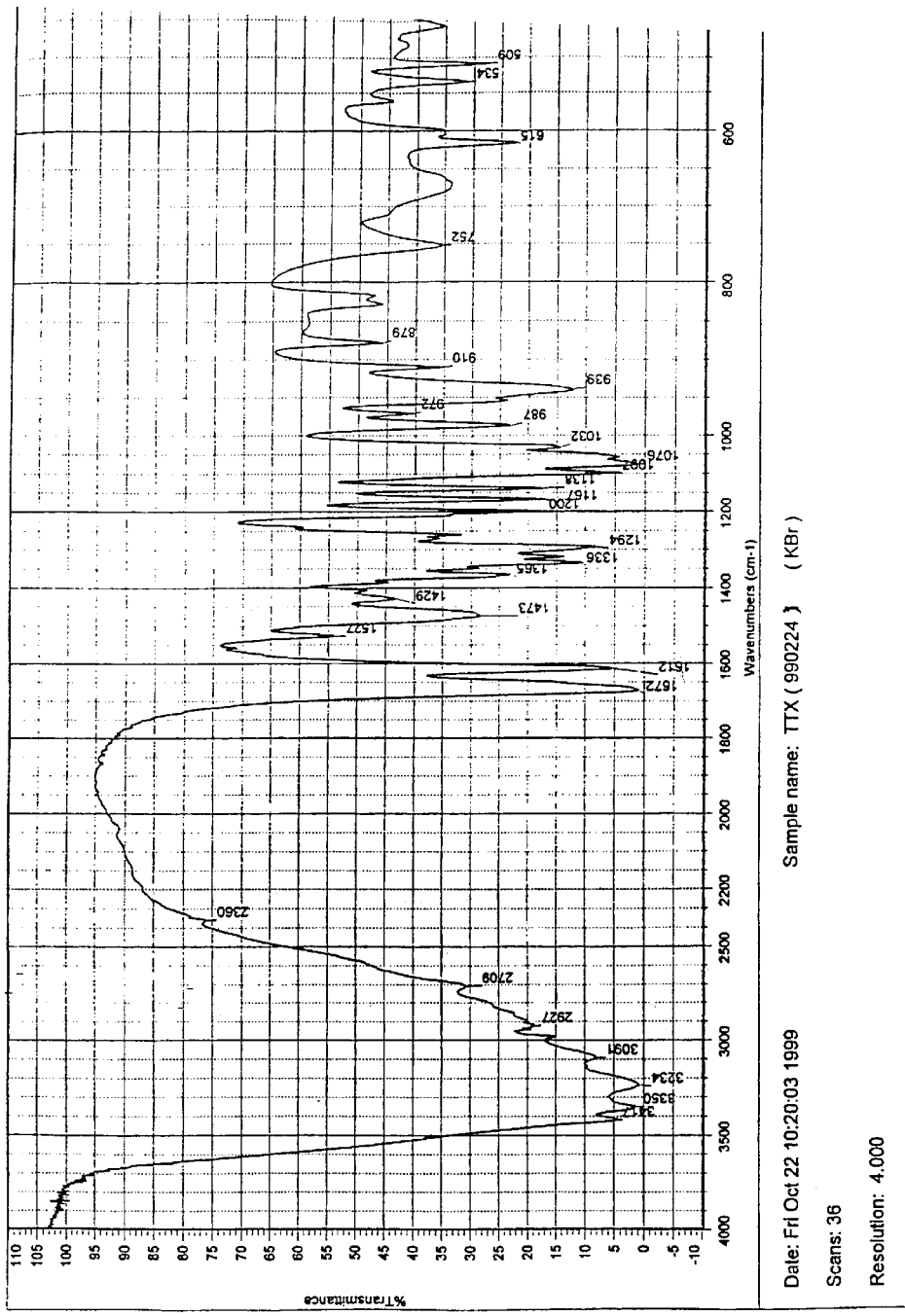

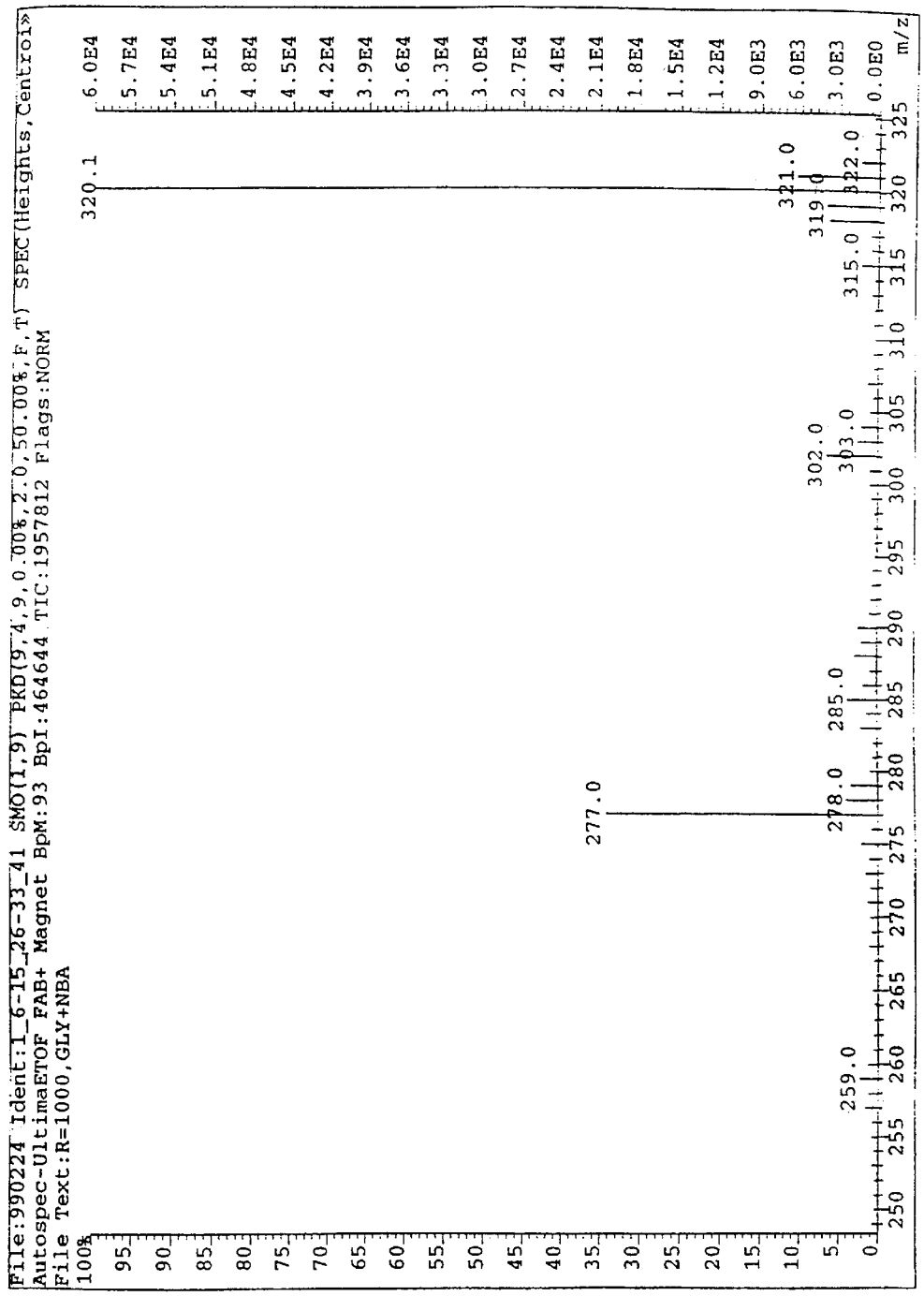
Figure 13. Mass spectrum of TTX (Batch 990224)

Figure 14. HPLC profile of TTX (Batch 990315)

Channel A

| Time | Area | Area % | Height | Height % |
|---|---|---|---|---|
| 11.593 | 5077 | 0.15 | 376 | 0.36 |
| 12.457 | 3421429 | 99.12 | 101998 | 98.99 |
| 16.680 | 25438 | 0.74 | 664 | 0.64 |
| Totals | 3451944 | 100.00 | 103038 | 100.00 |

Figure 15. HPLC profile of TTX (Batch 990315)
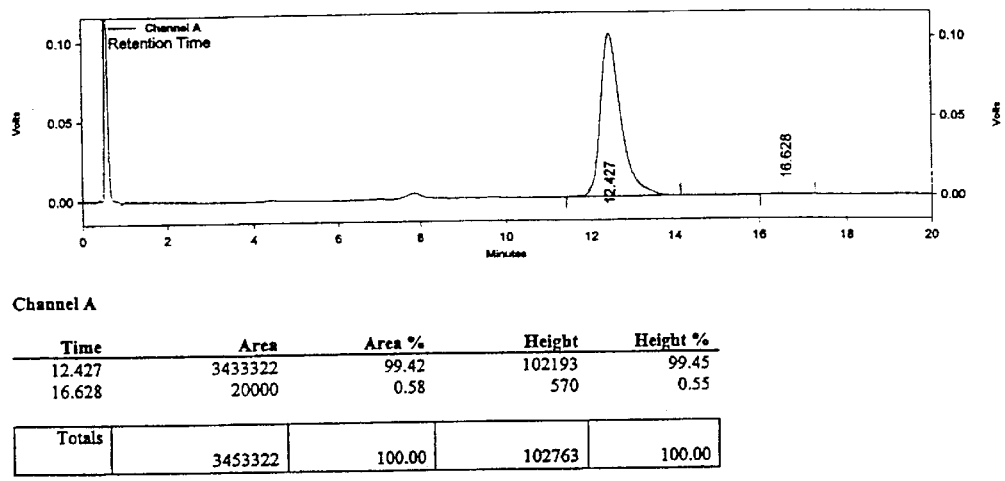

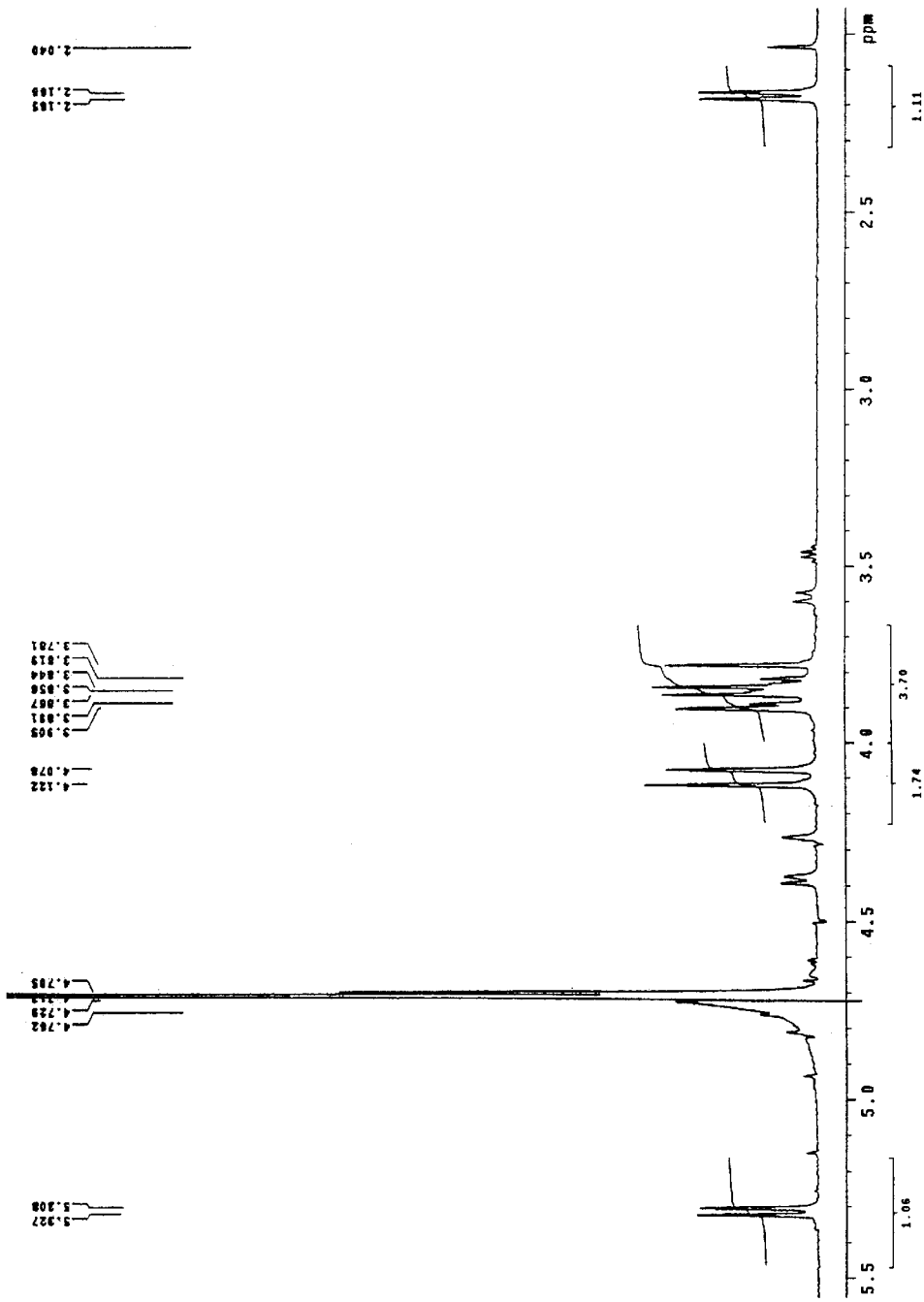
Figure 16. ¹H-NMR spectrum of TTX (Batch 990315)

Figure 17. UV absorption spectrum of TTX (Batch 990315)

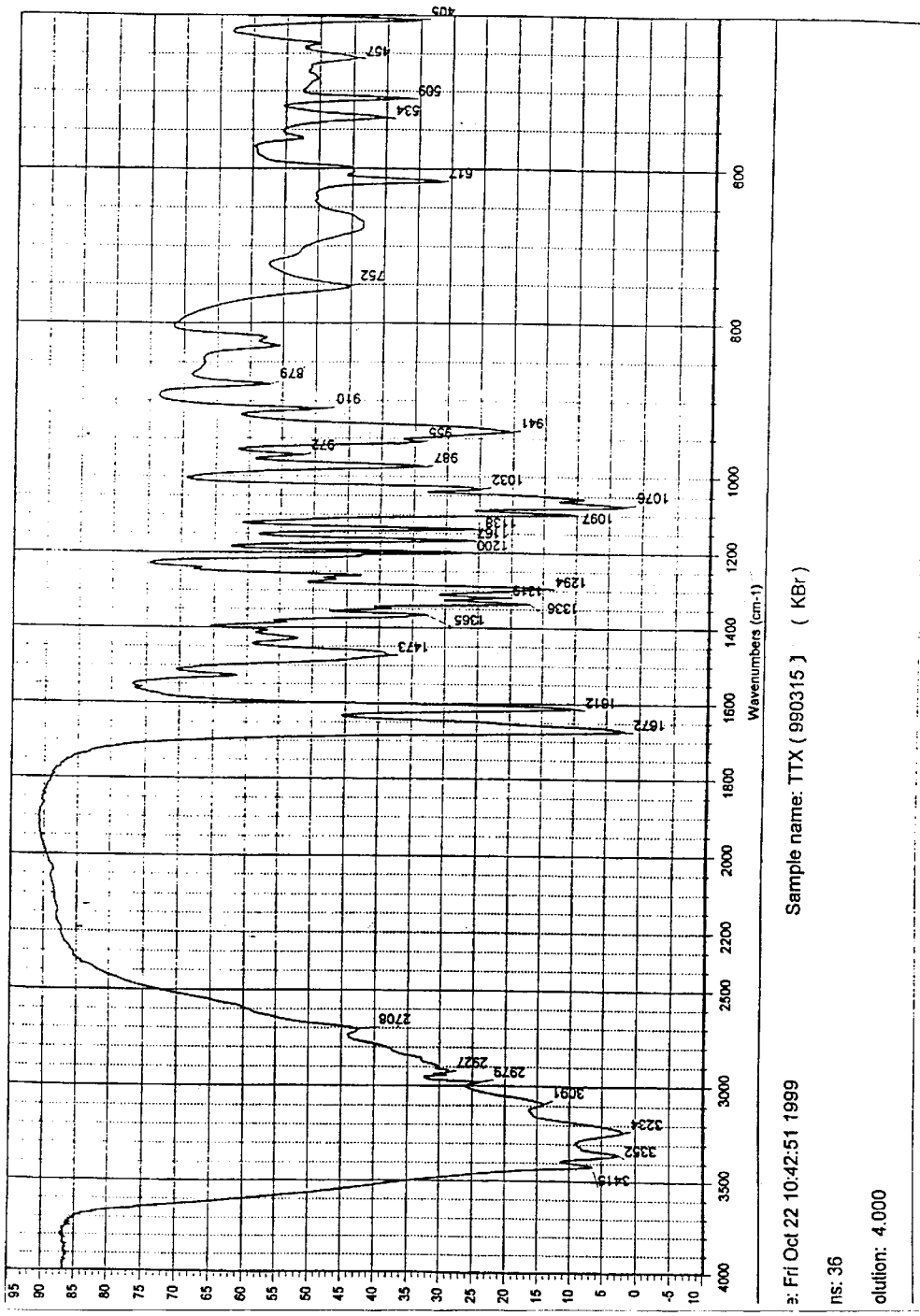
Figure 18. Infrared absorption spectrum of TTX (Batch 990315)

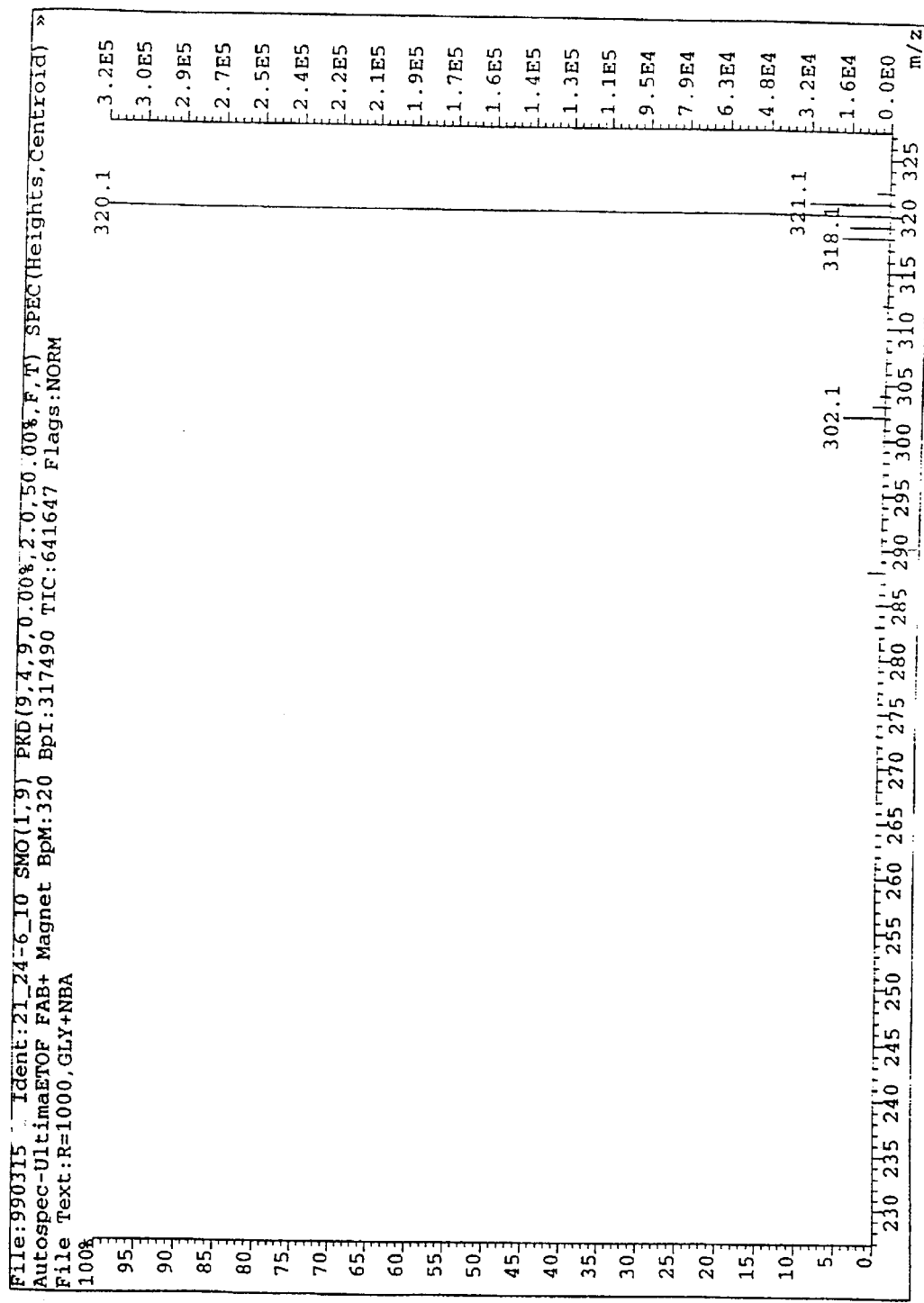
Figure 19. Mass spectrum of TTX (Batch 990315)

Figure 20. HPLC profile of TTX (Batch 990319)

Channel A

| Time | Area | Area % | Height | Height % |
|---|---|---|---|---|
| 12.354 | 4923715 | 99.59 | 148004 | 99.62 |
| 16.493 | 20201 | 0.41 | 572 | 0.38 |

| Totals | | | | |
|---|---|---|---|---|
| | 4943916 | 100.00 | 148576 | 100.00 |

Figure 21. HPLC profile of TTX (Batch 990319)
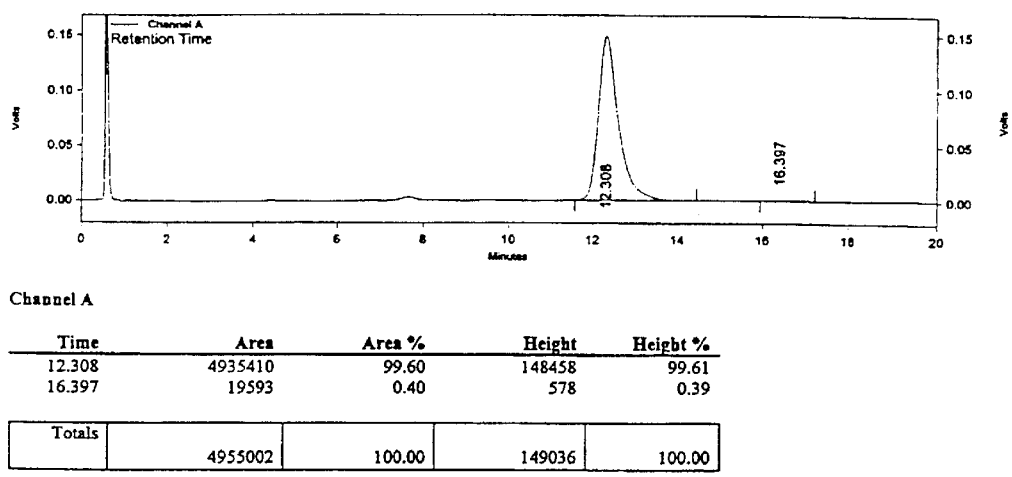
Channel A
| Time | Area | Area % | Height | Height % |
|---|---|---|---|---|
| 12.308 | 4935410 | 99.60 | 148458 | 99.61 |
| 16.397 | 19593 | 0.40 | 578 | 0.39 |
| Totals | | | | |
|---|---|---|---|---|
| | 4955002 | 100.00 | 149036 | 100.00 |

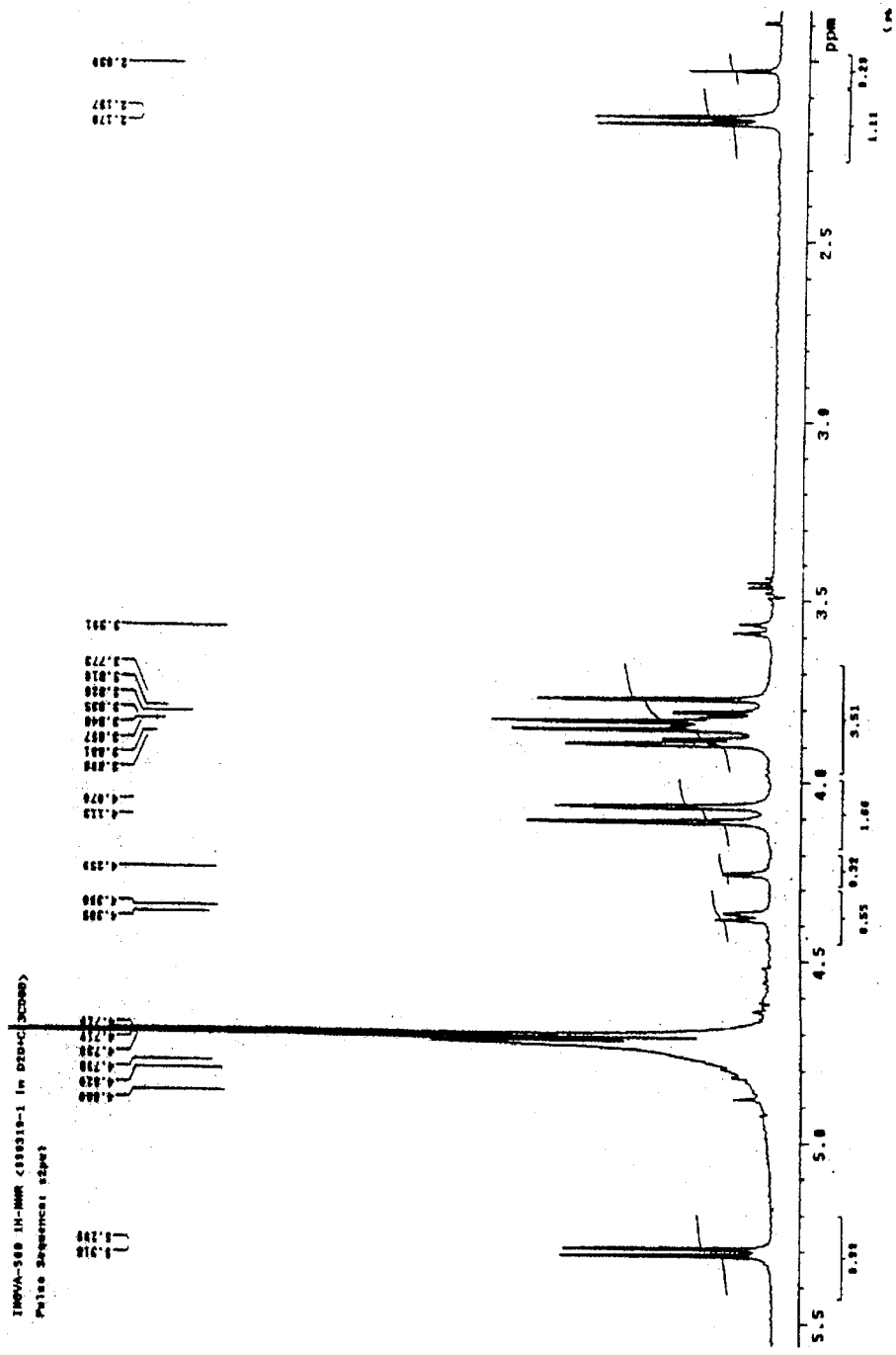
Figure 22. ¹H-NMR spectrum of TTX (Batch 990319)

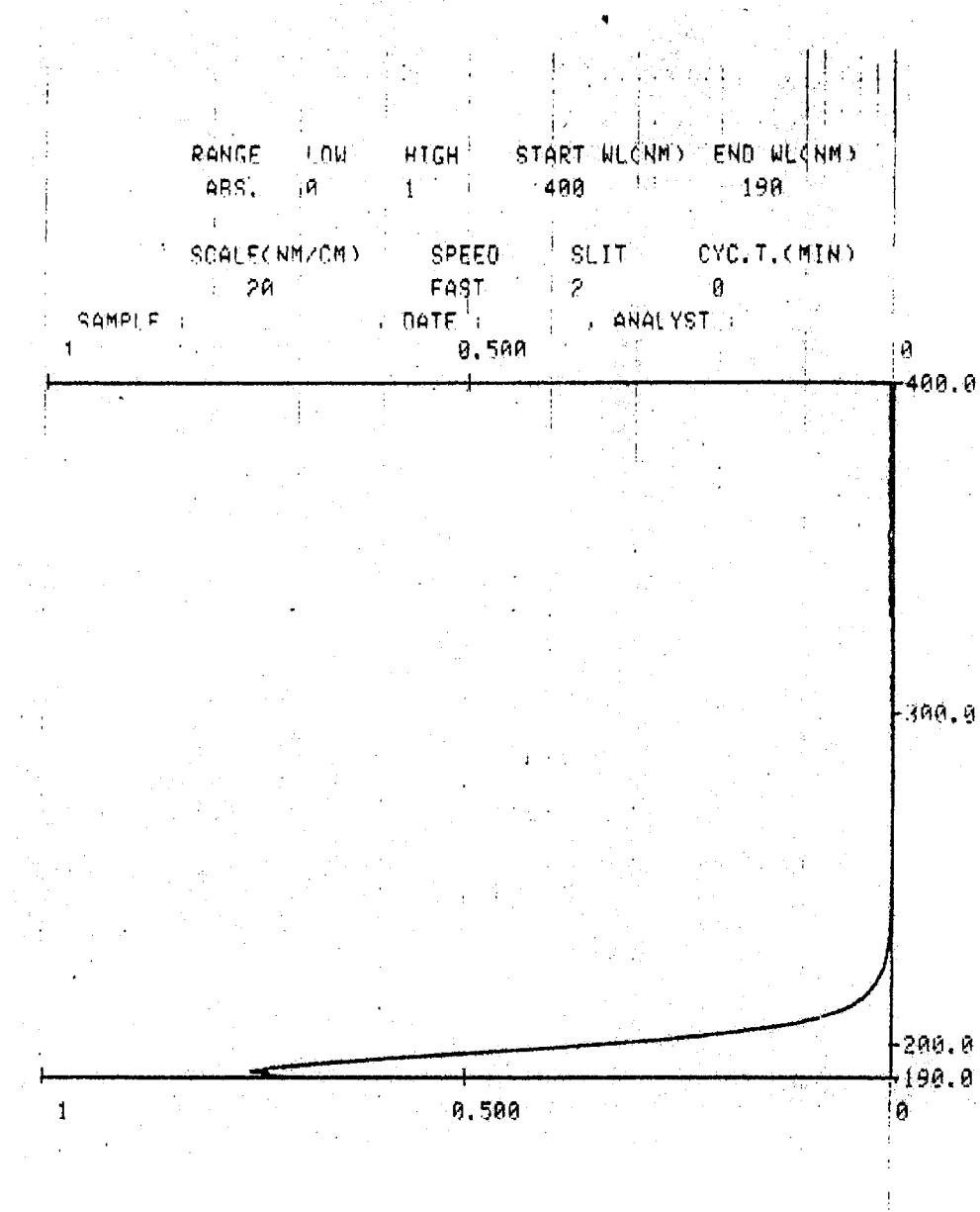
Figure 23. UV absorption spectrum of TTX (Batch 990319)

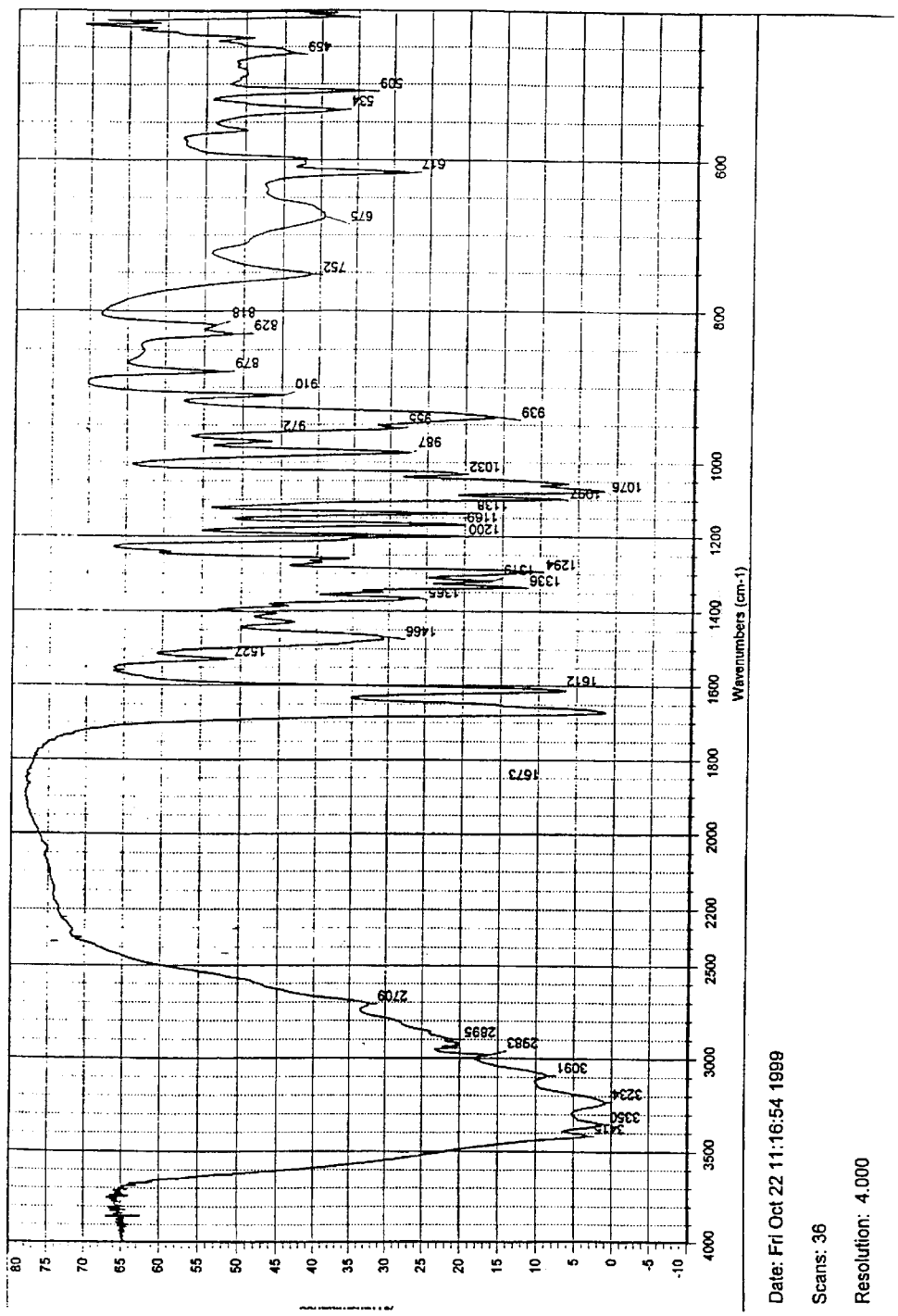
Figure 24. Infrared absorption spectrum of TTX (Batch 990319)

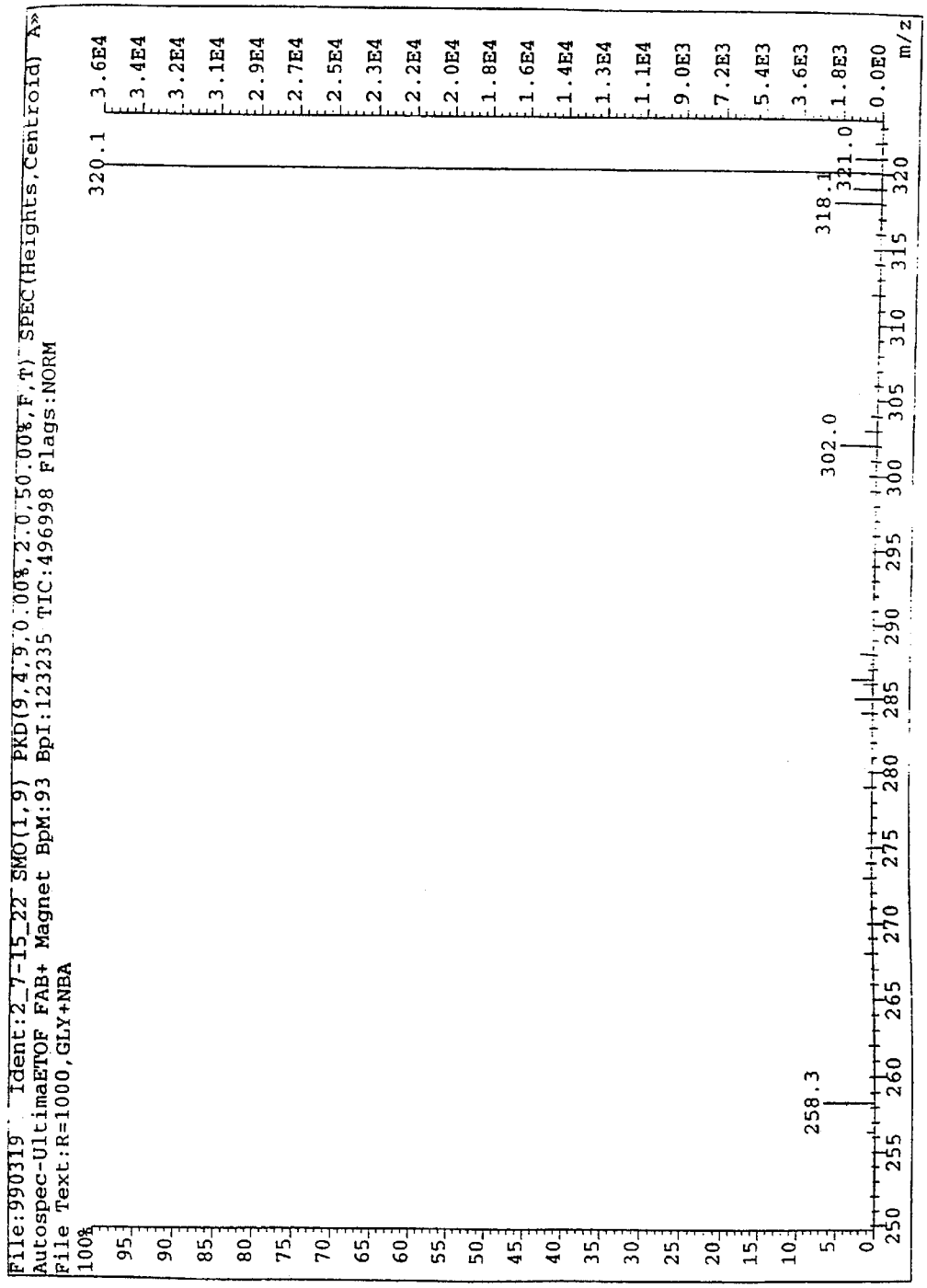
Figure 25. Mass spectrum of TTX (Batch 990319)

METHOD OF PURIFYING TETRODOTOXIN

FIELD OF INVENTION

The present invention relates to a chromoatographic method for obtaining tetrodotoxin of high purity.

BACKGROUND OF THE INVENTION

Tetrodotoxin is a nonprotein neurotoxin with potent activity. It is found in diverse animal species, including puffer fish, goby fish, newt, frogs and the blue-ringed octopus.

Tetrodotoxin (TTX) has a chemical formula of $C_{11}H_{17}N_3O_8$, and has a molecular weight of 319.28. The Merck Index, 10$^{th}$ Ed. (1983), states tetrodotoxin is the generic name for the compound octahydro-12-(hydroxymethyl)-2-imino-5,9:7,10a-dimethano-10aH-(1,3)dioxocino(6,5-d)-pyrimidine-4,7,10,11, 12-pentol, which has the following structure:

TTX molecule consists of a perhydroquinozoline group with a guanidine substituent and six hydroxyl groups. Pure TTX is a white crystalline powder, odorless and tasteless. It turns black around 220° C. without decomposition. TTX is soluble in acidic aqueous solution, but not soluble in organic solvents. The pKa (aqueous) of TTX is 8.76; it is thus a basic alkaloid. Strongly acidic aqueous solutions can decompose TTX, so usually TTX is dissolved in an aqueous solution of a weak organic acid. TTX is relatively thermally stable in neutral to weakly acidic solutions, but will be destroyed promptly in a strongly acidic or basic aqueous solution.

By HPLC, the toxin extracted from puffer fish has been determined to be a mixture of more than 10 analogs, among which tetrodotoxin is predominant, accounting for 70% to 80% of the mass of the extract. Three other major analogs are tetrodonic acid, 4-epi tetrodotoxin and 4-epi anhydrotetrodotoxin, which are only slightly different in chemical properties but significantly different in biological activities. For example, the toxicity of tetrodotoxin is 4500 mouse units/milligram; 4-epi tetrodotoxin, only 710 mouse units/milligram; 4-epi anhydrotetrodotoxin, only 92 mouse units/milligram. [1] A method to extract tetrodotoxin with high yield from the tissues of an organism (such as the puffer fish ovaries) is described in co-pending application Ser. No. 09/695,711 filed Oct. 25, 2000 (Attorney Docket No. 3519-01010P). The TTX obtained by this method typically has a purity of 80% or higher. The TTX product obtained by the method can be further purified to 96%, even 99% or higher, by way of the technology of the present invention. The present invention therefore provides material suitable for uses, such as pharmaceutical formulations, that might require tetrodotoxin of very high purity.

The refining of TTX from biological tissues or cell cultures involves two major tasks. The first is to remove from TTX those impurities that are not a toxin substance, that is, compounds other than TTX and its analogues. Thus, it is necessary to separate TTX from substances such as the residual amino acids, polypeptides, and proteins. These substances are so different in physical properties from TTX and its analogues that they can be easily removed by adding organic solvent or by dissolving TTX in, for example, acetic acid and then precipitating the TTX from a basic solution such as an ammonia solution. Copending application Ser. No. 09/695,711 filed Oct. 25, 2000 (Attorney Docket No. 3519-0101P) describes this process in detail.

The other task is to remove TTX analogues. Reverse phase ion-pairing HPLC, utilizing a phosphate buffer as the mobile phase, has been described as a method for separating TTX from related compounds.[3] It was reported in late 1990s that TTX, 4-epi-TTX and anhydro-4-epi-TTX can be separated using several types of columns. For example, Nakamura and Yasumoto [1] used a cation exchange column and citrate buffer. Yasumoto and Michishita [4] used a octyldecylsilane column with aqueous acetonitrile, heptaflurobutyric acid, NaOH system as the mobile phase.

SUMMARY OF THE INVENTION

The present invention resides in a method for chromatographic purification of TTX, preferably using high performance liquid chromatography (HPLC). The method employs an octadecylsilane reverse phase separation matrix and an aqueous alkyl sulphonate solution as the mobile phase.

BRIEF DESCRIPTION OF THE DRAWINGS

FIG. 3—HPLC profile of crude TTX (Batch 990705).

FIG. 4—HPLC profile of TTX reference (Sample 1).

FIG. 5—HPLC profile of TTX reference (Sample 1).

FIG. 6—HPLC profile of TTX reference (Sample 2).

FIG. 7—HPLC profile of TTX reference (Sample 2).

FIG. 8—HPLC profile of TTX (Batch 990224).

FIG. 9—HPLC profile of TTX (Batch 990224).

FIG. 10—$^1$H-NMR spectrum of TTX (Batch 990224).

FIG. 11—UV absorption spectrum of TTX (Batch 990224).

FIG. 12—Infrared absorption spectrum of TTX (Batch 990224).

FIG. 13—Mass spectrum of TTX (Batch 990224).

FIG. 14—HPLC profile of TTX (Batch 990315).

FIG. 15—HPLC profile of TTX (Batch 990315).

FIG. 16—$^1$H-NMR spectrum of TTX (Batch 990315).

FIG. 17—UV absorption spectrum of TTX (Batch 990315).

FIG. 18—Infrared absorption spectrum of TTX (Batch 990315).

FIG. 19—Mass spectrum of TTX (Batch 990315).

FIG. 20—HPLC profile of TTX (Batch 990319).

FIG. 21—HPLC profile of TTX (Batch 990319).

FIG. 22—$^1$H-NMR spectrum of TTX (Batch 990319).

FIG. 23 UV absorption spectrum of TTX (Batch 990319).

FIG. 24—Infrared absorption spectrum of TTX (Batch 990319).

FIG. 25—Mass spectrum of TTX (Batch 990319).

DETAILED DESCRIPTION OF THE INVENTION

The present method utilizes chromatography over an octadecylsilane matrix to purify TTX. Octadecylsilane (ODS) phases are bonded to silica or polymeric packings. Both monomeric and polymeric phases are available. Reverse phase chromatography columns packed with ODS matrices are available from a number of commercial suppliers.

The column is eluted using an aqueous solution of alkyl sulfonate. The sodium salt is preferred, but other salts, such as potassium or lithium, are acceptable. The alkyl sulfonate is preferably one having 3 to 10 carbon atoms and is also preferably an n-alkyl sulfonate. Heptane sulfonate is the most preferred alkyl sulfonate.

The alkyl sulfonate is present in the mobile phase in a concentration of from 0.005 to 0.05 molar, preferably from 0.01 to 0.04 molar.

The mobile phase can also include an alcohol. The alcohol is a lower saturated alcohol, preferably methanol or ethanol. When alcohol is included, the ratio of alcohol to alkyl sulfonate is in the range from 1:100 to 1:200, preferably from 1:150 to 1:200.

The elution is best performed as an isocratic elution. TTX is detected using ultraviolet absorbance, preferably at 201 nm. The TTX peak can be identified by retention time, calibrating the column using a standard purified TTX sample.

The purity of TTX in the final eluate collected after the process of the present invention can reach as high as 99.9%. Due to the conversion of TTX during storing and processing, however, the refined solid TTX still contains minimal analogues. In general, the purity of the refined TTX is above 96%, as easily observed from an analytical HPLC profile.

The Purification Process:

I. Pre-processing

Pre-processing is required only when the crude TTX starting material contains less than 80% tetrodotoxin. In order not to cause any damage to the chromatograph column, those impurities other than TTX and its analogues and perhaps a small amount of TTX analogs should be removed from crude starting material containing less than 80% tetrodotoxin.

Figure 1:
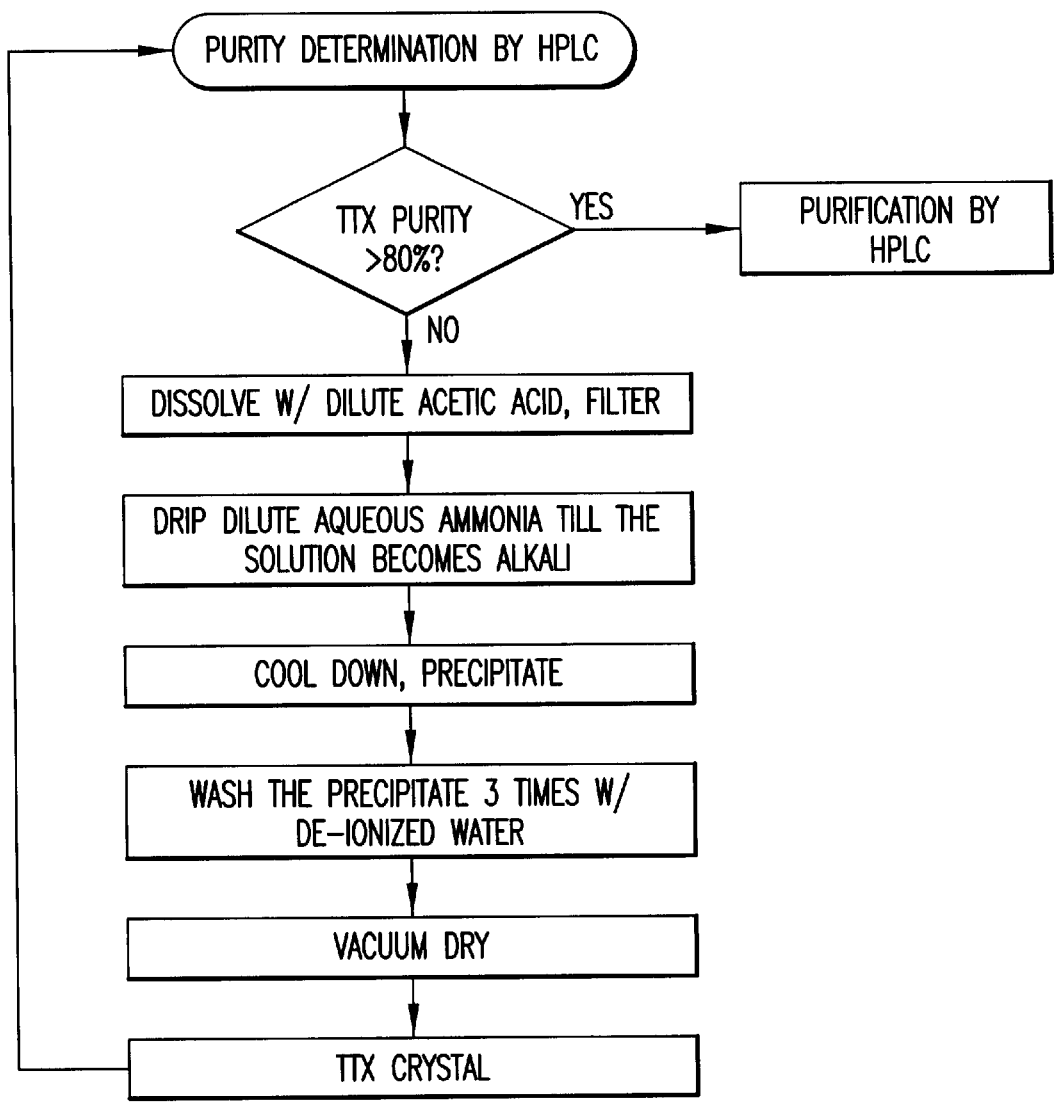
FIG. 1—A flow chart of pre-processing for TTX purification.
Figure 2:
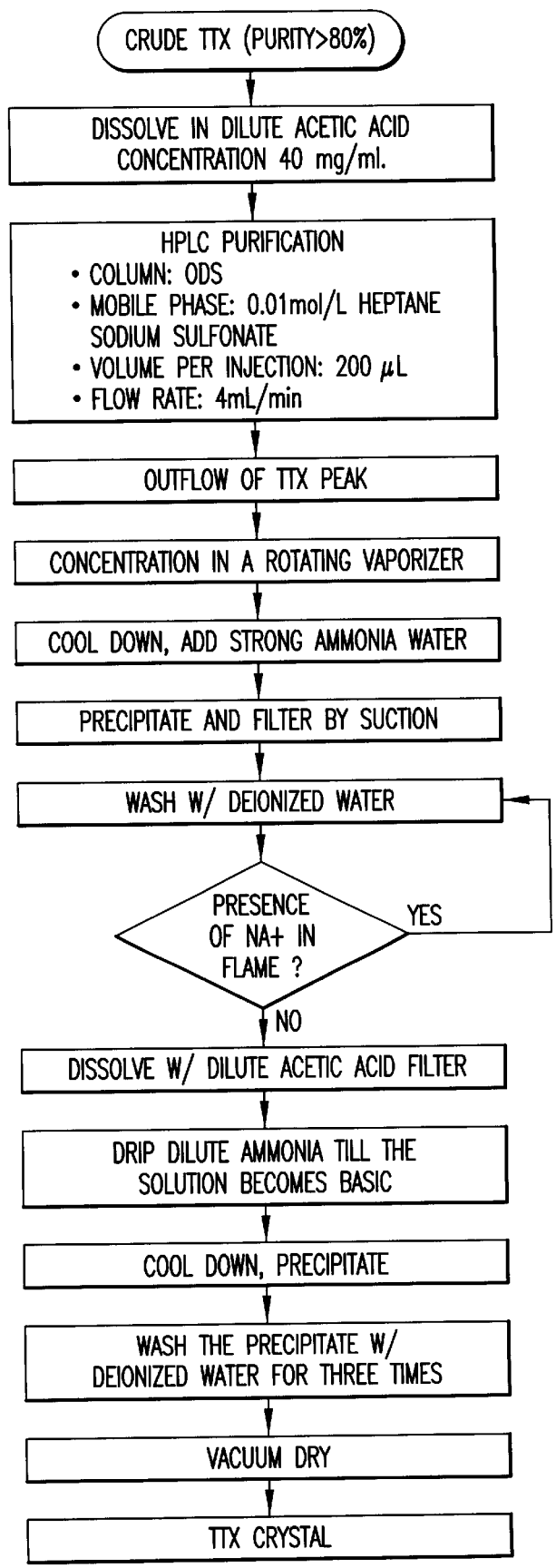
FIG. 2—A flow chart of TTX purification by HPLC.

Before further processing, the content of TTX in the starting material is determined. If the TTX content is less than 80%, the TTX can be recrystallized by adding an adequate amount of dilute acetic acid to dissolve most of the crude starting material, and then filtering to remove any insoluble material. Dilute aqueous ammonia can be added to make the solution alkaline. The solution is cooled and TTX will precipitate upon standing. The TTX is recovered by filtering. The recrystallized TTX is then washed with deionized water and dried. This process can be performed repeatedly so that the content of TTX can be raised over 80%. A flow chart of the pre-processing is shown in FIG. 1. This process can be varied, for example by use of weak organic acids other than acetic acid, or by use of amine bases other than ammonia.

Chromatographic Purification

Chromatograph conditions:

The chromatographic purification is performed using apparatus typical in the art and commercially available. The apparatus is employed as described above. An exemplary purification utilizing an HPLC system is described in the Examples.

The TTX sample is prepared for chromatography by dissolving the crude TTX in dilute weak acid. The acid is preferably an organic acid such as formic acid, acetic acid or propionic acid. However, inorganic acids can also be used such as phosphoric acid, sulfuric acid or hydrochloric acid. Acetic acid is the most preferred acid.

The concentration of the acid should be from 0.5 to 5%; the pH of the sample should be from pH 3 to 5.

The sample is typically dissolved to a concentration of TTX of from 40 to 160 mg/ml.

The column is equilibrated in the mobile phase. After the column reaches equilibrium, the TTX solution is applied quantitatively. The peak corresponding to the TTX peak, best determined by prior calibration of retention time using a standard purified TTX sample, is collected. If TTX and the impurities are not separated completely (i.e. baseline resolution of the peaks), it is suggested, not to collect those parts of eluates that manifest the impurity peaks overlapping those starting and ending parts of the TTX peak.

TTX can be purified to an extent as high as 99% by this method.

In a preferred embodiment, the chromatography is performed using a column having a diameter between 10–19 millimeters, the tetrodotoxin sample is applied in a volume of from 50 to 500 $\mu$L and the mobile phase has a flow rate of from 4 mL/minute to 10 mL/minute. Aqueous sodium heptane sulfonate, with or without an alcohol as a further ingredient, may be used as the mobile phase in this embodiment.

Precipitation and crystallization:

The TTX eluate can be further purified by concentration, e.g. using a rotary evaporator at a mildly warm temperature. After cooling, the pH is adjusted to an alkaline value, typically 8 to 9, by adding strong ammonia dropwise. TTX is precipitated under these conditions. The product is collected, typically by filtration or centrifugation.

EXAMPLE

The following example serves to illustrate the invention, but is in no way intended to limit the invention. Chromatograph and separation conditions:

| Instrument: | Waters 600 HPLC |
| --- | --- |
| Column: | ODS column (5$\mu$), 250 × 10 mm |
| Mobile phase: | 0.01 mol/L sodium heptane sulfonate solution |
| Detection: | UV detector detection wavelength 201 nm. |
| Flow-rate: | 4 mL/min. |
| Sample: | Crude TTX (containing 86.17% TTX, batch 990705) dissolved in 5% dilute acetic acid and water, concentration 40 mg/mL, sampling volume 200 $\mu$l each time. |

After the column was equilibrated with mobile phase, 200 $\mu$L TTX solution was injected quantitatively with a sample valve. The eluate peak containing TTX was collected, based upon the retention time of a TTX standard. The TTX eluate prepared and collected by HPLC was concentrated directly in a rotary evaporator at a mildly warm temperature to 10 mL. After it was cooled down, strong ammonia was added dropwise until the pH of the solution became alkaline, whereupon a large amount of TTX precipitated. The precipitate was collected by filtration using vacuum filtration through a ground glass funnel and washed with deionized water until there was no presence of a yellow flame, characteristic of the presence of sodium ion, in a flame check. Next, the precipitate was dissolved in dilute acetic acid (5%), filtered, and neutralized with dilute 8% ammonia. Then the solution was adjusted to alkaline pH so as to precipitate TTX. The precipitate was filtered out, then washed with water and dried. This acetic acid dissolving and ammonia-precipitating treatment was repeated. Subsequently, the washed and dried TTX crystals were put into a vacuum desiccator and dried again to constant weight. The refined product was collected and the purity determined by HPLC under rigorous quantitative conditions as described below:

Instrument and Reagents

Instrument: Beckman HPLC (USA, including Model 125 pump.

Model 166 variable wavelength detector and Gold Nouveau chromatography workstation).

Reference sample of TTX, Batch No. S–1, provided by Nanning Maple Leaf Pharmaceuticals.

Reagents: Heptane sodium sulfonate (Kasei Kogyo Co., Ltd., Tokyo, Japan), methanol (Merck). Water: de-ionized water.

Preparation of Solution

Accurately weigh 10 mg of tetrodotoxin and put into a 25 mL volumetric flask, add 0.02% acetic acid solution and dilute to the mark, shake and mix well. Inject 20 µl of the solution into the chromatograph according to the conditions described.

Chromatographic conditions and system

Column: ODS (5 µm), 4.6 mm×250 mm

Column temperature: 30° C.

Mobile phase: 0.01 M heptane sodium sulfonate (pH 5.30) - Methanol (100:1)

Flow rate: 1.5 ml/min

Detection wavelength: 205 nm

Precision

Inject 20 µl of the sample solution into the chromatograph, record chromatogram and measure the peak area. Repeat the procedure six times. The RSD of the tetrodotoxin peak area is 0.2% (n=6).

Stability

Start timing when the sample solution is prepared, inject 20 µl of sample solution into the chromatograph at 0, 0.5, 1.0, 2.0, 4.0 8.0 12.0 hr, record their chromatograms, and calculate the peak area of tetrodotoxin. The RSD was 0.7%.

Linearity and Limit of Detection

Accurately weigh 12.625 mg of the reference tetrodotoxin and put into a 100 ml volumetric flask, add 0.02% acetic acid solution and dilute to the mark, shake and mix well. Precisely inject 100, 80, 40, 20, 8, and 4 µl of the solutions into the chromatograph and record their chromatograms. Use the peak area as the vertical axis and the sampling amount as the horizontal axis to plot the standard calibration curve. The linear regression equation is y=3403.91+243226x with a linear range of 12.625~0.505 µg and a correlation coefficient of 0.9999.

The limit of detection is 0.01 ng based upon the signal to noise ratio (S/N≧3).

Accuracy

Accurately take five 5.0 mL portions of the sample solution (0.505 mg/mL), put into 10 mL volumetric flasks, then add in 4.0 ml of the reference solution (0.4184 mg/mL), respectively. Take two more portions of 5.0 mL sample solutions and put into 10 mL volumetric flasks, and add the mobile phase to the mark, shake and mix well. Inject 20 µl of the above solutions into the chomatograph, respectively. The average recovery is calculated to be 100.2% with a RSD of 0.9% (n=5).

| Injection Number | Amount injected | Amount measured (µg) | Recovery (%) |
|---|---|---|---|
| 1 | 4.04 | 4.03 | 99.75 |
| 2 | 4.04 | 4.10 | 101.48 |
| 3 | 4.04 | 4.07 | 100.74 |
| 4 | 4.04 | 4.02 | 99.50 |
| 5 | 4.04 | 4.02 | 99.50 |

Sample Content Determination

Accurately weigh 10 mg sample and put into a 25 mL volumetric flask, add in 0.02% acetic acid solution and dilute to the mark, inject 20 µl of the solution into the chromatograph, record the chromatogram and measure the peak area. The sample content can be calculated based upon the standard calibration curve. The results for the samples of the three batches are as follows (See FIGS. 8, 9, 14, 15, 20 and 21.):

| Batch number | Content (%) |
|---|---|
| 990224-1 | 99.38 |
| 990315-1 | 98.66 |
| 990319-1 | 99.11 |

The results of three purity examinations are listed as follows:

TABLE 2

Recovery and quality of refined TTX (by HPLC refining method)

| Batch number | Weight of starting crude* (mg) | Weight of refined product (mg) | Average yield (%) | Determined purity** (%) |
|---|---|---|---|---|
| 990224[a] | 120 | 70 | 58 | 96.85 |
| 990315[b] | 130 | 78 | 60 | 96.77 |
| 990319[c] | 212 | 130 | 61 | 96.31 |

Specifications and standards of chemical reagents

| | | |
|---|---|---|
| Sodium heptane sulfonate | Purity > 98.0% | Kasei Kogyo Co. Ltd., Tokyo, Japan |
| Ammonia | AR GB 631-89 | The Chemical Reagent Factory of Guangxi Normal College, China |
| Glacial acetic acid | AR GB 670-90 | Nanning Chemical Reagent Factory of Guangxi, China |
| De-ionized water | Self-defined standard | Nanning Maple Leaf Pharmaceutical Co., Ltd., China |

References

Articles of the scientific and patent literature are cited in this document. All such articles are hereby incorporated by reference in their entirety and for all purposes by such citation.

[1]. Munetomo Nakamura and Takeshi Yasumoto, Toxicon, 23, 271–276(1985).

[2]. T. Goto, Y. Kishi, S. Tahahashi and Y. Hirata Tetrahedron, 21, 2059–2088(1965).

[3]. Huilang Zhao, Xiuming Xin, Guoqiang Dan, Wenxiu Wang, P. R. China J. Hygiene Examination, Vol 49, pp263–265 (1994).

[4]. Takeshi Yasumoto and Tooru Michishita, Agric. Biol. Chem, Vol. 49, pp. 3077–3080 (1985).

We claim:

1. A method of purifying tetrodotoxin comprising the steps of:
    a) preparing a sample by dissolving a substance comprising tetrodotoxin in a weak organic acid;
    b) applying the tetrodotoxin solution to a chromatography column comprising an octyldecylsilane stationary phase and chromatographically separating the sample using a mobile phase comprising an aqueous alkyl sulfonate solution; and
    c) collecting a fraction that comprises tetrodotoxin.

2. The method of claim 1, further comprising a step d) crystallizing the tetrodotoxin from the fraction obtained in step c.

3. The method of claim 1, wherein in step a, the dilute organic acid is acetic acid and has a concentration between 0.5%–5% by volume.

4. The method of claim 1, wherein in step b, the alkyl sulfonate solution has a concentration between 0.005–0.04 mol/L.

5. The method of claim 1, wherein in step b, the alkyl sulfonate solution is a sodium heptane sulfonate solution.

6. The method of claim 1, wherein in step b, the mobile phase is a mixture of sodium heptane sulfonate solution and an alkyl alcohol.

7. The method of claim 6, wherein the alkyl alcohol is ethanol or methanol.

8. The method of claim 6, wherein the sodium heptane sulfonate solution has a concentration between 0.005–0.04 mol/L.

9. The method of claim 6, wherein the mixture of sodium heptane sulfonate solution and alcohol is in a proportion between 200:1 and 100:1.

10. The method of claim 7, wherein the mixture of sodium heptane sulfonate solution and alcohol is in a proportion between 150:1 and 100:1.

11. The method of claim 10, wherein the alcohol is methanol.

\* \* \* \* \*